(12) United States Patent
Karube et al.

(10) Patent No.: US 9,963,410 B2
(45) Date of Patent: May 8, 2018

(54) METHOD FOR PRODUCING 1-CHLORO-2,3,3-TRIFLUOROPROPENE

(71) Applicant: DAIKIN INDUSTRIES, LTD., Osaka (JP)

(72) Inventors: Daisuke Karube, Osaka (JP); Satoshi Ohishi, Osaka (JP); Michiaki Okada, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days. days.

(21) Appl. No.: 15/553,592

(22) PCT Filed: Feb. 23, 2016

(86) PCT No.: PCT/JP2016/055267
§ 371 (c)(1),
(2) Date: Aug. 25, 2017

(87) PCT Pub. No.: WO2016/136744
PCT Pub. Date: Sep. 1, 2016

(65) Prior Publication Data
US 2018/0044268 A1    Feb. 15, 2018

(30) Foreign Application Priority Data

Feb. 27, 2015  (JP) .................. 2015-037827

(51) Int. Cl.
| C09K 5/04 | (2006.01) |
| C07C 17/25 | (2006.01) |
| C07C 17/42 | (2006.01) |
| C07C 17/16 | (2006.01) |

(52) U.S. Cl.
CPC .............. *C07C 17/25* (2013.01); *C07C 17/16* (2013.01); *C07C 17/42* (2013.01); *C09K 5/04* (2013.01)

(58) Field of Classification Search
CPC ......... C07C 17/16; C07C 17/25; C07C 21/18; C07C 19/10; C09K 5/04; C07B 61/00

USPC .................................. 570/156, 155; 252/67
See application file for complete search history.

(56) References Cited

U.S. PATENT DOCUMENTS

| 5,629,461 | A * | 5/1997 | Yasuhara | .............. C07C 17/206 |
| | | | | 570/166 |
| 2012/0161063 | A1 * | 6/2012 | Singh | ...................... C08J 9/144 |
| | | | | 252/67 |
| 2016/0023974 | A1 * | 1/2016 | Bonnet | ................... C07C 21/18 |
| | | | | 252/182.12 |

FOREIGN PATENT DOCUMENTS

| JP | 2010-529111 | 8/2010 |
| JP | 2010-235569 | 10/2010 |
| JP | 2012-509857 | 4/2012 |
| JP | 5056946 | 10/2012 |
| JP | 2013-504658 | 2/2013 |
| WO | 94/14737 | 7/1994 |
| WO | 2009/035130 | 3/2009 |
| WO | 2010/060868 | 6/2010 |
| WO | 2011/031697 | 3/2011 |
| WO | WO-2017018412 A1 * | 2/2017 ............. C07C 17/25 |

OTHER PUBLICATIONS

CAS reg. No. 133117-29-0, Apr. 12, 1991. (Year: 1991).*
International Search Report dated May 24, 2016 in International Application No. PCT/JP2016/055267.
Matsuo, "Fine Chemicals Division Web Magazine", Daikin Industries, Ltd., Aug. 2013, 3 pages, with machine translation.
CAS Registry No. 438547-44-5, Jul. 15, 2002, 5 pages.

* cited by examiner

*Primary Examiner* — Douglas J McGinty
(74) *Attorney, Agent, or Firm* — Wenderoth, Lind & Ponack, L.L.P.

(57) ABSTRACT

The present invention provides a method for producing 1233yd that enables high conversion of the starting compound and high selectivity of 1233yd. The present invention provide a method for producing 1-chloro-2,3,3-trifluoropropene (1233yd), comprising the step of dehydrofluorinating 3-chloro-1,1,2,2-tetrafluoropropane (244ca).

9 Claims, No Drawings

METHOD FOR PRODUCING 1-CHLORO-2,3,3-TRIFLUOROPROPENE

TECHNICAL FIELD

The present invention relates to a method for producing 1-chloro-2,3,3-trifluoropropene.

BACKGROUND ART 1-chloro-2,3,3-trifluoropropene (1233yd) is expected to serve as a useful compound forming a medium for heat transfer.

In recent years, 2,3,3,3-tetrafluoropropene (1234yf), 1,3,3,3-tetrafluoropropene (1234ze), etc., are widely used as media for heat transfer, and there are many disclosures of methods for producing these compounds.

However, a specific method for producing 1233yd has not yet been extensively studied. There is thus a demand for the establishment of a method for producing 1233yd that enables high conversion of the starting compound and high selectivity of 1233yd.

CITATION LIST

Patent Literature

PTL 1: JP5056946B

SUMMARY OF INVENTION

Technical Problem

An object of the present invention is to provide a method for producing 1233yd that enables high conversion of the starting compound and high selectivity of 1233yd.

PTL 1 does not disclose a method for producing 1233yd, but discloses a method for producing a chlorine-containing fluoroalkene by dehydrofluorination of a chlorine-containing fluoroalkane. As a specific example, PTL 1 discloses a method for producing 1-chloro-2,3,3,3-tetrafluoropropene ($CF_3CF$=$CHCl$) (1224yd) by dehydrofluorination of 3-chloro-1,1,1,2,2-pentafluoropropane ($CF_3CF_2CH_2Cl$) (235cb).

For example, 1,1,2,3,3,3-hexafluoropropane ($CF_3CHFCHF_2$) (236ea) is considered to be used as a reactant for performing a dehydrofluorination reaction. It is, however, known that when such a compound, which has multiple hydrogen atoms that can be eliminated during the dehydrofluorination reaction, is used, multiple compounds are produced, resulting in reduced selectivity of the desired product.

When 1233yd is produced using a dehydrofluorination reaction, a starting compound represented by the composition formula: $C_3H_3F_4Cl$, in which one H and one F are added to the composition formula of 1233yd: $C_3H_2F_3Cl$, is used. Examples of starting compounds include 3-chloro-1,1,2,2-tetrafluoropropane ($CHF_2CF_2CH_2Cl$) (244ca) and 3-chloro-1,1,2,3-tetrafluoropropane ($CHF_2CHFCHFCl$) (244ea). When 1233yd is produced using, among such starting compounds, a starting compound having multiple hydrogen atoms that can be eliminated during the dehydrofluorination reaction, the following by-products may be produced, depending on the combination of the starting compound used and the position of hydrogen eliminated.

Examples of such by-products include structural isomers 3-chloro-1,1,2-trifluoropropene ($CF_2$=$CFCH_2Cl$) (1233yc), 3-chloro-1,2,3-trifluoropropene ($CHF$=$CFCHFCl$) (1233ye), 1-chloro-1,3,3-trifluoropropene ($CHF_2CH$=$CFCl$) (1233zb), 3-chloro-1,1,3-trifluoropropene ($CF_2$=$CHCHFCl$) (1233zc), and the like. Examples further include 1,2,3,3-tetrafluoropropene ($CHF_2CF$=$CHF$) (1234ye), which is obtained by dehydrochlorination from such a starting compound as described above, and the like. Since the molecular weights of these by-products and the molecular weight of 1233yd are almost the same, the by-products are believed to have boiling points close to the boiling point of 1233yd. It is therefore considered difficult to separate and purify these by a common technique such as distillation. There is thus a need for a method for producing 1233yd with high selectivity in which, for example, 1233yc is unlikely to be produced.

Solution to Problem

The present inventors conducted extensive research to achieve the above object, and found that when 3-chloro-1,1,2,2-tetrafluoropropane (244ca) is dehydrofluorinated, 1233yd can be produced with high selectivity while achieving high conversion of the starting compound. The inventors further found that this method achieves the unexpected effects that the production of 1233yc, which is a highly toxic by-product that is difficult to separate from 1233yd, is suppressed and that the selectivity of 1233yd is extremely high. The inventors conducted further research based on these findings, thereby accomplishing the present invention. Specifically, the invention provides the following method for producing 1233yd.

Item 1. A method for producing 1-chloro-2,3,3-trifluoropropene (1233yd), comprising the step of dehydrofluorinating 3-chloro-1,1,2,2-tetrafluoropropane (244ca).

Item 2. The method according to Item 1, wherein the dehydrofluorination is performed in the presence of an accelerator.

Item 3. The method according to Item 1 or 2, wherein the dehydrofluorination is performed in a liquid phase in the presence of a catalyst.

Item 4. The method according to any one of claims 1 to 3, wherein the products are continuously withdrawn.

Item 5. The method according to any one of Items 1 to 4, further comprising the step of chlorinating 2,2,3,3-tetrafluoropropanol to produce the 3-chloro-1,1,2,2-tetrafluoropropane (244ca).

Item 6. The method according to Item 5, wherein molecular chlorine, thionyl chloride, oxalyl chloride, phosphoryl chloride, or phosphorus chloride is used as a chlorinating agent in the chlorination.

Item 7. The method according to Item 5 or 6, comprising the steps of chlorinating 2,2,3,3-tetrafluoropropanol to produce the 3-chloro-1,1,2,2-tetrafluoropropane (244ca) and dehydrofluorinating the 244ca in a single reactor.

Item 8. A composition comprising 1-chloro-2,3,3-trifluoropropene (1233yd) and at least one compound selected from the group consisting of 1-chloro-3,3-difluoropropyne ($CHF_2C$≡$CCl$), 1-chloro-1,3,3-trifluoropropene (1233zb), and 3-chloro-1,1,1,3-tetrafluoropropane (244fa), the total amount of the at least one compound selected from the group consisting of 1-chloro-3,3-difluoropropyne, 1233zb, and 244fa being 5 vol % or less.

Item 9. The composition according to Item 8, which is a medium for heat transfer.

Advantageous Effects of Invention

The production method of the present invention enables high conversion of the starting compound and the production of 1233yd with high selectivity, and suppresses the production of 1233yc as a by-product.

DESCRIPTION OF EMBODIMENTS

The present invention is described in detail below. The main propanes and propenes relating to the invention are defined in Table 1.

TABLE 1

| Code | Chemical Name | Chemical Formula |
|---|---|---|
| 244ca | 3-chloro-1,1,2,2-tetrafluoropropane | $CHF_2CF_2CH_2Cl$ |
| 1233yd | 1-chloro-2,3,3-trifluoropropene | $CHF_2CF=CHCl$ |
| 1233yc | 3-chloro-1,1,2-trifluoropropene | $CH_2ClCF=CF_2$ |
| 1233zb | 1-chloro-1,3,3-trifluoropropene | $CHF_2CH=CFCl$ |
| 244fa | 1-chloro-1,3,3,3-tetrafluoropropane | $CHFClCH_2CF_3$ |

The present invention relates to a method for producing 1233yd, comprising the step of dehydrofluorinating 244ca. 1233yd can be suitably used as a medium for heat transfer.

Starting Compound

In the present invention, 244ca is used as a starting compound. 244ca can be synthesized by various methods. For example, 244ca can be produced by chlorinating 2,2,3,3-tetrafluoropropanol using a chlorinating agent.

The chlorination reaction of 2,2,3,3-tetrafluoropropanol can be performed in either a gas phase or a liquid phase. Examples of chlorinating agents that can be suitably used include molecular chlorine, thionyl chloride, oxalyl chloride, phosphoryl chloride, phosphorus chloride, and the like.

Additionally, 2,2,3,3-tetrafluoropropanol can be produced by reacting tetrafluoroethylene with methanol.

Dehydrofluorination Reaction Step

The dehydrofluorination reaction of 244ca is performed according to the following reaction formula.

$$CHF_2CF_2CH_2Cl \longrightarrow CHF_2CF=CHCl + HF$$
$$(244ca) \qquad\qquad (1233yd)$$

In the present invention, the dehydrofluorination reaction can be performed in a medium, and a medium that contains water is generally used. The water-containing medium may also contain one or more media other than water, such as an organic solvent. Examples include aromatic hydrocarbons such as benzene, toluene, and (o-, m-, or p-) xylene; aliphatic hydrocarbons such as hexane, octane, and nonane; ethers such as diethyl ether and tetrahydrofuran; and the like. Among these, hydrophobic organic solvents such as aromatic hydrocarbons and aliphatic hydrocarbons are preferred, and more specifically, solvents with a boiling point of 100° C. or more, such as toluene and xylene, are preferred.

The entire amount of the medium is generally 1 to 15 parts by weight, preferably 2 to 10 parts by weight, per part by weight of 244ca. In the medium, the weight ratio of water to the other medium is generally 100:0 to 10:90, and preferably 70:30 to 30:70.

In an embodiment of the present invention, the dehydrofluorination reaction can be performed in the presence of an accelerator.

The dehydrofluorination reaction of 244ca in the present invention can be performed either in a batch mode or in a flow mode in which 244ca used as a starting compound is continuously fed to a reactor and the products are continuously withdrawn from the reactor. When the product stays the reaction site, the dehydrofluorination reaction can further proceed. In view of this, the dehydrofluorination reaction is preferably performed in a flow mode.

244ca can be produced by the known method described above. Reaction equipment for converting the starting material for 244ca into 244ca can be connected to reaction equipment for converting 244ca into 1233yd to continuously produce 1233yd from the starting material for 244ca. Further, a reaction for converting the starting material for 244ca into 244ca and a reaction for converting 244ca into 1233yd can be performed in a single reactor. From the viewpoint of reaction efficiency, operation efficiency, equipment costs, energy costs, etc., the reactions are preferably performed in a single reactor.

Accelerator and Catalyst

It is preferred that either an accelerator or a catalyst for facilitating defluorination, or both, be present in a reaction site where the dehydrofluorination reaction in the present invention is performed.

The accelerator can increase the rate of reaction from the starting compound to 1233yd by eliminating fluorine from the starting compound and reacting with the fluorine or hydrogen fluoride. Due to this, when a catalyst is present in the reaction site, the activity, lifetime, etc., of the catalyst can be improved.

The accelerator is preferably present in an amount at least equivalent to the starting compound, and the amount of accelerator is particularly preferably about 1 to 3 equivalents, relative to the starting compound.

The accelerator is not particularly limited, and an alkali or base compound, such as a metal hydroxide or a metal oxide, can be used. When the dehydrofluorination reaction is performed in a liquid phase, it is preferable to use such an alkali or base compound.

The alkali or base compound used as an accelerator is used for facilitating the dehydrofluorination reaction to form a carbon-carbon double bond. Either an organic base or an inorganic base can be used, as long as it is water soluble.

Examples of organic bases include trialkylamines such as triethylamine and diisopropylethylamine. Examples of inorganic bases include alkali metal hydroxides such as potassium hydroxide and sodium hydroxide; alkaline earth metal hydroxides such as calcium hydroxide; metal oxides such as magnesium oxide; and the like. Among these, alkali metal hydroxides are preferable, and potassium hydroxide is more preferable.

Among organic bases or inorganic bases, sodium hydroxide, potassium hydroxide, calcium hydroxide, potassium carbonate, or sodium carbonate is preferably used as an accelerator, and potassium hydroxide is particularly preferable.

The amount of the alkali or base compound used as an accelerator is generally 1 to 5 mol, and preferably 1.5 to 3.5 mol, per mol of the starting compound. The conversion of the starting compound and the selectivity of 1233yd tend to improve as the amount of the base increases.

Examples of catalysts include Brønsted acids such as sulfonic acid and phosphoric acid, Lewis acids such as metal oxides and metal halides, and the like.

When the dehydrofluorination reaction is performed in a gas phase, although it is not particularly limited, it is preferable to use a catalyst. For example, at least one member selected from the group consisting of activated carbons, metals, metal oxides can be used. Also usable is aluminum oxide, chromium oxide, tin oxide, iron chloride, aluminum fluoride, fluorinated aluminum oxide, fluorinated chromium oxide, magnesium oxide, magnesium fluoride, fluorinated magnesium oxide, lanthanum oxide, fluorinated lanthanum oxide, lanthanum fluoride, nickel, nickel oxide, a catalyst obtained by mixing or combining two or more of these, or the like. These catalysts may be supported on a carrier. Among these catalysts, fluorinated aluminum oxide and fluorinated chromium oxide are particularly preferable.

Phase-Transfer Catalyst and Surfactant

In the present invention, the medium described above, which contains either water or an organic solvent (in particular, a hydrophobic organic solvent), or both, can be used in the dehydrofluorination reaction. When the reaction medium forms two phases, the reaction medium may also contain a phase-transfer catalyst, a surfactant, etc., in order to facilitate the reaction between the substances in the two phases, in addition to the accelerator or catalyst mentioned above.

The phase-transfer catalyst has the action of transferring a starting compound into a phase in which a reaction occurs. When the dehydrofluorination reaction is performed in a liquid phase in which water is present, i.e., in a reaction system in which an aqueous phase and an organic phase coexist and in which the reactant is present in the two phases, it is particularly preferable to use a phase-transfer catalyst in order to facilitate the reaction between the reactant in the two phases.

The phase-transfer catalyst is not particularly limited. Examples include quaternary ammonium salts such as tetrabutylammonium bromide (TBAB), trimethylbenzylammonium bromide, triethylbenzylammonium bromide, and trioctylmethylammonium chloride (TOMAC); phosphonium salts such as tetrabutylphosphonium chloride (TBPC); crown ethers such as 15-crown 5 and 18-crown 6; and the like. Examples also include known substances such as alkylammonium salts, carboxylic acid salts, and alkylsulfonic acid salts. Of these, quaternary ammonium salts are preferable, and, for example, tetrabutylammonium bromide, trioctylmethylammonium bromide, Aliquat 336 (registered trademark), or the like can be suitably used.

When a phase-transfer catalyst is used, the amount of the phase-transfer catalyst is 0.05 to 10 wt %, and preferably 0.08 to 5 wt %, based on the weight of water used as a medium.

Examples of surfactants include nonionic surfactants such as fatty acid diethanolamides; cationic surfactants such as alkyl triethyl ammonium salts; anionic surfactants such as monoalkyl sulfuric acid salts; amphoteric surfactants such as alkylcarboxybetaines; and the like. Of these, amphoteric surfactants are preferable from the viewpoint of heat resistance.

When a surfactant is used, the amount of the surfactant is generally 0.05 to 10 wt %, and preferably 0.08 to 5 wt %, based on the weight of water used as a medium.

Reaction Conditions

The dehydrofluorination reaction can be performed in either a liquid phase or a gas phase, and it is preferred that the dehydrofluorination reaction be performed in a liquid phase.

The reaction temperature for the dehydrofluorination reaction is not particularly limited, and is generally in the range of about 0 to 500° C. When the reaction is performed in a liquid phase, the reaction temperature is preferably in the range of about 0 to 150° C., and more preferably about 30 to 100° C. When the reaction is performed in a gas phase, the reaction temperature is preferably in the range of 100 to 450° C. Both when the reaction is performed in a liquid phase and when the reaction is performed in a gas phase, an excessively high reaction temperature is not preferable because the produced 1233yd may further react and the selectivity of dehydrofluorination may decrease, resulting in a reduction in the yield and the selectivity.

The reaction time for the dehydrofluorination reaction is not particularly limited. In the liquid-phase reaction, the conversion can be increased by increasing the reaction time, and in the gas-phase reaction, the conversion can be increased by increasing the contact time. However, an excessively long reaction time or contact time is inefficient because the produced 1233yd further reacts to decrease the yield and the selectivity, and the equipment becomes larger than necessary. It is thus necessary to select the appropriate reaction time or contact time also in view of other conditions such as the amount of the reaction accelerator added and the reaction temperature. When the reaction is performed in a liquid phase, the reaction time is generally 4 to 8 hours. When the reaction is performed in a gas phase, the contact time is generally about 1 to 100 seconds.

The pressure for the dehydrofluorination reaction is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa.

Actions

The present invention enables high conversion of the starting compound and the production of 1233yd with high selectivity, and can suppress the production of 1233yc, i.e., a by-product, that is expected, from the position of hydrogen to be eliminated in view of the structure of the starting compound 244ca, to be produced. Moreover, 1233yd can be obtained efficiently in a simple manner using the starting compound that is easily available, while suppressing production costs and equipment costs.

EXAMPLES

An Example is given below to clarify the features of the present invention. The invention, however, is not limited to this Example.

Example 1

12 g of 244ca was mixed with an aqueous alkaline solution obtained by mixing 17 g of potassium hydroxide, 23 g of water, and 0.18 g of a quaternary ammonium salt (Aliquat 336(registered trademark)), which is a phase-transfer catalyst, and the mixture was heated to 100° C. in a flask and subjected to a reaction for 8 hours. The fraction was collected and analyzed by gas chromatography. The results showed that the conversion of 244ca was 90% and the selectivity of 1233yd was 94.8%.

All of the other products were derived from 1233yd. The results showed 1.6% for 1-chloro-3,3-difluoropropyne ($CHF_2C \equiv CCl$), 2.1% for 1233zb, and 0.2% for 244fa. The isomer 1233yc was not produced.

The invention claimed is:

1. A method for producing 1-chloro-2,3,3-trifluoropropene (1233yd), comprising the step of dehydrofluorinating 3-chloro-1,1,2,2-tetrafluoropropane (244ca),
   wherein the dehydrofluorination is performed in a liquid phase for a reaction time of 8 hours or less or is performed in a gas phase for a contact time of 100 seconds or less, and
   wherein the products are continuously withdrawn.

2. The method according to claim 1, wherein the dehydrofluorination is performed in a liquid phase in the presence of an accelerator.

3. The method according to claim 1, wherein the dehydrofluorination is performed in the presence of a catalyst.

4. The method according to claim 1, wherein the dehydrofluorination is performed in a liquid phase at a temperature in the range of about 0 to 150° C.

5. The method according to claim 1, further comprising the step of chlorinating 2,2,3,3-tetrafluoropropanol to produce the 3-chloro-1,1,2,2-tetrafluoropropane (244ca).

6. The method according to claim 5, wherein molecular chlorine, thionyl chloride, oxalyl chloride, phosphoryl chloride, or phosphorus chloride is used as a chlorinating agent in the chlorination.

7. The method according to claim 5, comprising the steps of chlorinating 2,2,3,3-tetrafluoropropanol to produce the 3-chloro-1,1,2,2-tetrafluoropropane (244ca) and dehydrofluorinating the 244ca in a single reactor.

8. A composition comprising 1-chloro-2,3,3-trifluoropropene (1233yd), 1-chloro-3,3-difluoropropyne ($CHF_2C \equiv CCl$), 1-chloro-1,3,3-trifluoropropene (1233zb), and 3-chloro-1,1,1,3-tetrafluoropropane (244fa),
wherein each of the 1233yd, 1-chloro-3,3-difluoropropyne, 1233zb and 244fa are present in the composition, and
wherein the total amount of the 1-chloro-3,3-difluoropropyne, 1233zb, and 244fa is 5 vol % or less.

9. The composition according to claim 8, which is a medium for heat transfer.

* * * * *